US005866756A

United States Patent [19]

Giros et al.

[11] Patent Number: 5,866,756

[45] Date of Patent: *Feb. 2, 1999

[54] DOPAMINE TRANSPORTER KNOCKOUT MICE

[75] Inventors: Bruno Giros, Chatillon; Mohamed Jaber, Merignac, both of France; Marc G. Caron, Hillsborough, N.C.

[73] Assignee: Duke University, Durham, N.C.

[ * ] Notice: This patent issued on a continued prosecution application filed under 37 CFR 1.53(d), and is subject to the twenty year patent term provisions of 35 U.S.C. 154(a)(2).

[21] Appl. No.: 724,405

[22] Filed: Oct. 2, 1996

Related U.S. Application Data

[60] Provisional application No. 60/004,695 Oct. 2, 1995.

[51] Int. Cl. [6] ............................ C12N 5/00; C12N 15/00

[52] U.S. Cl. .................. 800/2; 800/DIG. 1; 800/DIG. 3; 435/172.3; 424/9.1; 424/9.2

[58] Field of Search ............................ 800/2, DIG. 1–4; 435/172.3; 514/44, 2; 424/9.1

[56] References Cited

U.S. PATENT DOCUMENTS 5,447,948 9/1995 Seibyl et al. ............................ 514/393

FOREIGN PATENT DOCUMENTS

WO 93/24628 12/1993 WIPO .

OTHER PUBLICATIONS

Simantov et al. Dopamine–induced apoptosis in human neuronal cells–inhibition by nucleic acids antisense to the dopamine transporter. Neuroscience, vol. 74, No. 1, pp. 39–50, Sep. 1996.

Orkin et al. Report and recommendations of the panel to assess the NIH investment in research on gene therapy, Dec. 7, 1995.

Gura, T. Antisense has growing pains. Science, vol. 270, pp. 575–577, Oct. 27, 1995.

Mullins et al. Transgenesis in nonmurine species. Hypertension, vol. 22, No. 4, pp. 630–633, Oct. 1993.

Fassler et al. Knockout Mice: How to make them and why. The immunological approach. Int Arch Allergy Immunol, vol. 106, pp. 323–334, 1995.

Miner et al.; Behavioral Characterization of Mutant Dopamine Transporter and Mu Opiate Receptor Overexpression in Catecholaminergic Neurons of Transgenic Mice, *Society for Neuroscience Abstracts* 20(1–2):921 (1994), (abstract).

F. Hucho; The Neurochemistry of Parkinson's Disease—Comments on Present and Future Developments, *Journal Neural Transmission* [Suppl]46:59–65 (1995).

*Primary Examiner*—Jasemine C. Chambers
*Assistant Examiner*—Deborah J. R. Clark
*Attorney, Agent, or Firm*—Myers, Bigel, Sibley & Sajovec

[57] ABSTRACT

A recombinant rodent comprises cells containing a pair of genomic dopamine transporter protein alleles, wherein at least one of said alleles is incapable of expressing endogenous dopamine transporter protein. The rodent may be a homozygote, where both of said alleles are incapable of expressing endogenous dopamine transporter protein, or the rodent may be a heterozygote, and one of said alleles expresses endogenous dopamine transporter protein. The rodent is preferably a mouse.

7 Claims, 1 Drawing Sheet

DOPAMINE TRANSPORTER KNOCKOUT MICE

This invention was made with Government support under grant number NS19576 from the National Institutes of Health. The Government has certain rights to this invention.

This application claims the benefit of U.S. provisional application No. 60/004,695, filed on 02 Oct., 1995.

FIELD OF THE INVENTION

This invention relates to methods of increasing spontaneous motor activity in a subject in need of such treatment, particularly subjects afflicted with Parkinson's disease or tardive dyskinesia.

BACKGROUND OF THE INVENTION

Dopamine is involved in the control of motor function, cognition and affect (A. Dahlstrom and K. Fuxe, *Acta Physiol. Scand.* 232, 1–55 (1965); U. Ungerstedt, Acta Physiol. Scand. 367, 1–48 (1970)). Imbalance in the dopamine system is believed to be involved in such conditions as schizophrenia (T. Crow, Brit. *J. Psychiatry* 137, 383–386 (1980); Fibiger, in : The Mesolimbic dopamine system : From motivation to action, 615–37 (Eds. P. Willner and J. Scheel-Krger 1991)), Parkinson's disease (H. Ehringer and O. Hornykiewitz, *Klin. Wochenschr.* 38, 1236–1239 (1960), tardive dyskinesia and drug addiction (R. Wise and P. P. Rompre, *Ann. Rev. Psychol.* 40, 191–225 (1989); G. Koob and F. Bloom, *Science* 242, 715–723 (1988); G. DiChiara et al., *Proc. Natl Acad. Sci. U.S.A.* 85, 5272–5278 (1998)).

The dopamine transporter, a member of the large family of $Na^+/Cl^-$ dependent transporters, aids in terminating dopaminergic neurotransmission by rapid reuptake of dopamine (B. Giros and M. Caron, *Trends Pharmacol. Sci.* 14, 43–49 (1993). It is a major target of the psychostimulant drugs cocaine and amphetamine (B. Giros and M. Caron, *Trends Pharmacol. Sci.* 14, 43–49 (1993); M. Ritz et al., *Science* 237, 1219–1223 (1987)), but its overall role in vivo is still poorly understood.

SUMMARY OF THE INVENTION

A first aspect of the present invention is a recombinant rodent comprising cells containing a pair of genomic dopamine transporter protein alleles, and wherein at least one of said alleles is incapable of expressing endogenous dopamine transporter protein. The rodent may be a homozygote., where both of said alleles are incapable of expressing endogenous dopamine transporter protein, or the rodent may be a heterozygote, and one of said alleles expresses endogenous dopamine transporter protein.

A further aspect of the present invention is a method of upregulating spontaneous motor activity in a subject in need of such treatment. The method comprises inhibiting dopamine transporter function (i.e., dopamine reuptake mediated by the dopamine transporter protein) in the subject by an amount effective to enhance spontaneous motor activity in that subject. The method may be carried out by any suitable means, such as by administering a dopamine transporter blocker to said subject in an amount effective to enhance spontaneous motor activity. Suitable subjects include those afflicted with Parkinson's disease and those afflicted with tardive dyskinesia, particularly drug-induced tardive dyskinesia.

A still further aspect of the present invention is the use of a dopamine transporter inhibitor for the preparation of a medicament for enhancing spontaneous motor activity in that subject, as described above.

DETAILED DESCRIPTION OF THE INVENTION

Figure 1:
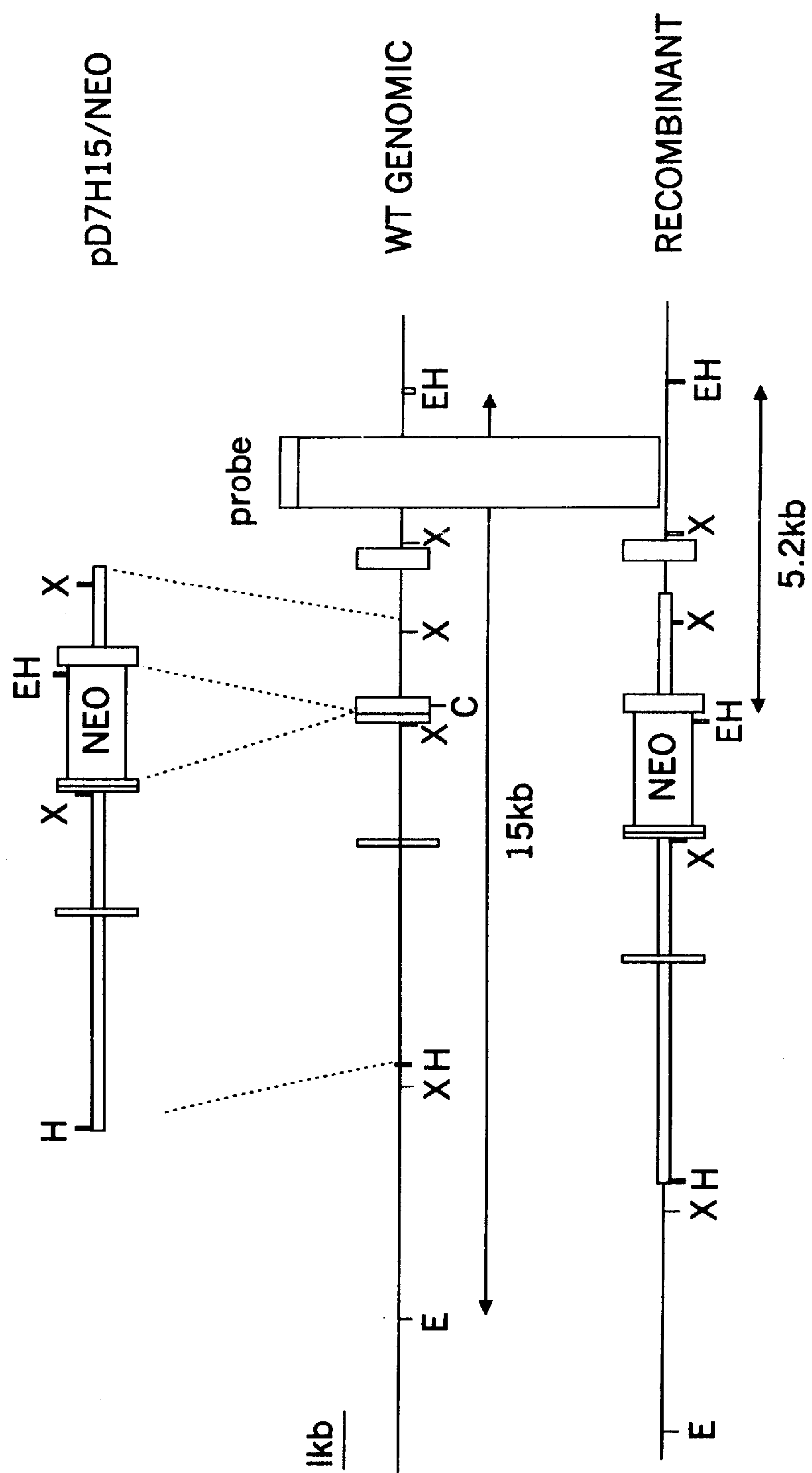
FIG. 1 shows the targeting of the mouse DAT gene in ES cells and mice. Gene structures and restriction maps for the DAT targeting construct (pD7H15/Neo), wild-type and recombinant are shown. Black and open boxes represent coding and untranslated exons, respectively. Arrow lines indicate the EcoRI restriction fragment sizes for wild-type and recombinant DNA. Restriction sites are : C, ClaI; E, EcoRI; H, HindIII; X, XbaI. The probe used for Southern analysis is shown as a thick black line.

We herein describe the first gene inactivation of a member of the $Na^+/Cl^-$-dependent transporter family. We provide direct in vivo evidence that the dopamine transporter may represent the most crucial functional determinant of neurotransmitter tone in the central nervous system identified to date. The functional ablation of the dopamine transporter in the mouse produces a phenotype in which homozygote animals display a marked increase in spontaneous locomotor activity. This phenotype is presumably a reflection of the prolonged availability of dopamine at the synapse, as effects of similar magnitude are observed following complete blockade of the transporter with maximal doses of psychostimulants (G. DiChiara and A. Imperato, *Proc. Natl Acad. Sci. U.S.A.* 85, 5272–5278 (1998); B. Giros and M. Caron, *Trends Pharmacol. Sci.* 14, 43–49 (1993); M. Ritz et al., *Science* 237, 1219–1223 (1987); M. Jaber et al., *Neuroscience,* 65, 1041–1050 (1995)). This hyperlocomotion phenotype is apparent even in light of major adaptive decreases in the mRNAs for the D1 and D2 receptors, the main targets of synaptic dopamine responsiveness. This phenotype is even more impressive if one considers that levels of dopamine may be markedly lower in homozygote animals. Indeed, as seen by immunoblotting and immunohistochemistry, tyrosine hydroxylase, the rate limiting enzyme of dopamine synthesis, is reduced by more than 80%. in dopamine neurons and projections. In addition, the observation that heterozygote animals have certain characteristics which are intermediate between wild type and homozygote mice, reinforces the notion of a fundamental role for the dopamine transporter in the maintenance of normal dopaminergic neurotransmission.

The properties of the DAT knockout mice make them an attractive animal model for the study and development of drugs for the management of dopaminergic dysfunction. However, the most exciting consequences of these data are in the development of new therapeutic strategies for common neurological disorders. For example, these data indicate that targeting of the DAT with high affinity antagonists (J. Boja et al. *Mol. Pharmacol.* 47, 779–786 (1995)) in illnesses such as Parkinson's disease, where the effective levels of dopamine are markedly decreased, (H. Ehringer and O., Hornykiewitz, *Klin. Wochenschr.* 38, 1236–1239 (1960)) have beneficial clinical consequences.

Our results further demonstrate that the DAT, in addition to its proposed role in the reinforcing properties of the psychostimulants cocaine and amphetamine, (M. Ritz et al. *Science* 237, 1219–1223 (1987)) represents the primary target for their locomotor effects. Since cocaine, and to a lesser extent amphetamine, interact with other monoamine transporters, the DAT homozygote and heterozygote animals should prove an excellent model to elucidate complex behavioral paradigms such as reward, addiction and tolerance properties of these drugs.

Animals suitable for carrying out the present invention are, in general, rodent species. Rat and mouse are preferred, and the mouse is most preferred. Animals in every stage of development, including juvenile, adolescent, and adult, are included in this description, with adult animals particularly preferred.

"Knockout" animals refers to animals whose native or endogenous DAT allele or alleles have been disrupted by homologous recombination and which produce no functional DAT of their own. Knockout animals may be produced in accordance with techniques known in the art, particularly by means of in vivo homologous recombination, M. Capechi, *Science* 244, 1288–1292 (1989), in light of the known sequence for DNA encoding the DAT. See, e.g., A. Eshleman et al., *Molec. Pharmacol.* 45, 312–316 (1994). DAT knockout animals of species other than mice can be produced by variation of the procedures carried to produce Apo E knockout mice that will be apparent to those skilled in the art.

Animals described in the present invention are animals having at least one allele incapable of expressing endogenous dopamine transporter protein (DAT), and include both the heterozygous or homozygous forms (e.g., DAT+/− and DAT −/−). Animals may be chimeric animals or animals in which essentially all cells are recombinant. Preferably at least the brain cells are recombinant.

Animals of the present invention are useful in a variety of screening assays, as discussed below. In such assays, the compound being screened may be administered to the animal by any suitable means, including orally and parenterally (e.g., by subcutaneous injection). The particular activity detected in the animal (i.e., neuroleptic, antischizophrenic, control of substance abuse, neuropharmacological, appetite modulating, aggressive behavior modulating, and addictive activities) may be detected in accordance with techniques known to those skilled in the art of neuropharmacology.

A method of screening a compound for neuroleptic activity comprises administering a test compound to a recombinant animal as given above, and then detecting the presence or absence of neuroleptic activity in said animal. The method is particularly useful wherein the neuroleptic activity is antischizophrenic activity.

A method of screening a compound for activity for the control of substance abuse (i.e., inhibiting or treating addictive behavior) comprises administering a test compound to a recombinant animal (preferably homozygous) as given above, and then detecting the presence or absence of activity for the control of substance abuse in the animal. Substance abuses such as amphetamine abuse and cocaine abuse (i.e., amphetamine craving and cocaine craving) are particularly preferred categories of substance abuse for which compounds useful for the treatment thereof may be screened by the instant method.

A method useful as a negative control for screening a compound for norepinephrine or serotonin transporter activity comprises administering a test compound to a recombinant animal (preferably homozygous) as given above, and then detecting the presence or absence of neuropharmacological activity for the compound in the animal.

A method of screening a compound for appetite modulating activity comprises administering a test compound to a recombinant animal (preferably homozygous) as given above, and then detecting the presence or absence of appetite modulating activity in the animal. The activity screened for may be either activity in increasing or decreasing appetite.

A method of screening a compound for aggressive behavior modulating activity comprises administering a test compound to a recombinant animal (preferably homozygous) as given above, and then detecting the presence or absence of aggresive behavior modulating activity in the animal. The activity screened for may be either activity in increasing or decreasing aggressive behavior.

A method of screening a compound for substance abuse potential (i.e., reinforcing activity) comprises administering a test compound to a heterozygous recombinant animal as given above, and then detecting the presence or absence of addictive behavior with respect to the compound in the animal (i.e., the finding that the animal develops a craving for that compound, or that the administration of that compound is a positive reinforcement for that animal). The presence of addictive behavior indicating the compound has a potential for substance abuse.

As noted above, a further aspect of the present invention is a method of upregulating spontaneous motor activity in a subject in need of such treatment. The method may be carried out on human subjects or on animal subjects for veterinary purposes. Suitable subjects include those afflicted with Parkinson's disease and those afflicted with tardive dyskinesia, particularly drug-induced tardive dyskinesia. A variety of dopamine transporter inhibitors (also called dopamine uptake inhibitors; herein referred to as active compounds) of diverse structure are known. See, e.g., S. Berger, U.S. Pat. No. 5,217,987; J. Boja et al., *Molec. Pharmacol.* 47, 779–786 (1995); C. Xu et al., *Biochem. Pharmacol.* 49, 339–50 (1995); B. Madras et al., *Eur. J. Pharmacol.* 267, 167–73 (1994); F. Carroll et al., *J. Med. Chem.* 37, 2865–73 (1994); A. Eshleman et al., *Molec. Pharmacol.* 45, 312–16 (1994); R. Heikkila and L. Manzino, *Eur. J. Pharmacol.* 103, 241–8 (1984). Dopamine transporter inhibitors are, in general, ligands that bind in a stereospecific manner to the dopamine transporter protein. Examples of such compounds are:

(1) tricyclic antidepressants such as buprion, nomifensine, and amineptin;

(2) 1,4-disubstituted piperazines, or piperazine analogs, such as 1-[2-[bis(4-fluorophenyl) methoxy]ethyl]-4-(3-phenylpropyl)piperazine dihycrochloride (or GBR 12909), 1-[2-[bis(phenyl) methoxy]ethyl]-4-(3-phenylpropyl) piperazine dihydrochloride (or GBR12935), and GBR13069;

(3) tropane analogs, or (disubstituted phenyl) tropane-2 beta-carboxylic acid methyl esters, such as 3β-(4-fluorophenyl)tropane-2β-carboxylic acid methyl ester (or WIN 35,428) and 3β-(4-iodophenyl)tropane-2β-carboxylic acid isopropyl ester (RTI-121);

(4) substituted piperidines, or piperidine analogs, such as N-[1-(2-benzo[b]-thiophenyl) cyclohexyl] piperidine, indatraline, and 4-[2-[bis(4-fluorophenyl)methoxy]ethyl]-1-(3-phenylpropyl) piperidine (or O-526);

(5) quinoxaline derivatives, or quinoxaline analogs, such as 7-trifluoromethyl-4-(4-methyl-1-piperazinyl)pyrrolo[1,2-α]quinoxaline (or CGS 12066b); and (6) other compounds that are inhibitors of dopamine reuptake, such as mazindol, benztropine, bupropion, phencyclidine, methylphenidate, etc.

Because the DNA sequence of the dopamine transporter is known (See, e.g., A. Eshleman et al., supra), this sequence can be used to inhibit or downregulate dopamine transporter in animals by means of administering to the subject antisense oligonucleotides that bind to mRNA encoding the dopamine transporter in an amount effective to inhibit the function of the dopamine transporter, or by means of inhibiting dopamine transporter transcription by administering oligonucleotides that specifically bind to DNA encoding the dopamine transporter, and, by homologous recombination, inhibit the activity of the dopamine transporter.

The active compounds disclosed herein can be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, ptoluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Pharmaceutical compositions for use in the present method of increasing spontaneous motor activity include those suitable for inhalation, oral, rectal, topical, (including buccal, sublingual, dermal and intraocular) parenteral (including subcutaneous, intradermal, intramuscular, intravenous and intraarticular) and transdermal administration. The compositions may conveniently be presented in unit dosage form and may be prepared by any of the methods well known in the art. The formulations may conveniently be presented in unit dosage form and may be prepared by any of the methods well known in the art.

The dose of active compound will vary according to the the particular compound administered, the route of administration, the manner of formulation, the condition of the subject, and the dose at which adverse pharmacological effects occur. One skilled in the art will take such factors into account when determining dosage. Illustrative examples of typical dosages are, for methylphenidate, from 1 or 10 to 60 or 100 mg per subject daily, and for buproprion, from 10 or 100 to 450 or 1000 mg per subject daily.

In the manufacture of a medicament according to the invention (a "formulation"), active agents or the physiologically acceptable salts thereof (the "active compound") are typically admixed with, among other things, an acceptable carrier. The carrier must be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 99% by weight of the active compound. One or more active compounds may be incorporated in the formulations of the invention (e.g., the formulation may contain one or more additional antitubercular agents as noted above), which formulations may be prepared by any of the well known techniques of pharmacy consisting essentially of admixing the components, optionally including one or more accessory therapeutic ingredients.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder. Formulations for oral administration may optionally include enteric coatings known in the art to prevent degradation of the formulation in the stomach and provide release of the drug in the small intestine.

Formulations suitable for buccal (sublingual) administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, e.g., *Pharmaceutical Research* 3, 318 (1986)) and typically take the form of an optionally buffered aqueous solution of the active compound.

Those skilled in the art will appreciate numerous variations which may be made to the foregoing in carrying out the instant invention, which will be readily apparent from the literature concerning recombinant animals. See, e.g., H. Chen et al., PCT Application WO 95/03397; H. Chen et al., PCT Application WO 95/03402; C. Wood et al., PCT Application WO 91/00906; C. Lo et al., PCT Application WO 90/06992; P. Leder et al., U.S. Pat. No. 4,736,866; and T. Wagner et al., U.S. patent application No. 4,873,191.

The present invention is explained in greater detail by the following Examples. These examples are illustrative of the present invention, and are not to be construed as limiting thereof.

EXAMPLE 1

Targeting of the Mouse Dopamine Transporter

This example describes the production, by means of in vivo homologous recombination, of a strain of mice in which the gene encoding the dopamine transporter (DAT) has been disrupted.

A rat DAT cDNA probe comprising the N-terminal to the third transmembrane domain (B. Giros et al., *FEBS Letters* 295, 149–154 (1991)) was used to screen a mouse 129 Sv/J genomic library in accordance with known techniques (B. Giros et al., *Nature* 342, 923–926 (1989)). A 12 kb phage containing the first three exons of the mouse DAT gene was isolated, and a 7.5 kb HindIII fragment (from an internal site to a phage cloning site) was excises and subcloned into pGEM4Z. A EcoRI-SAlI-NotI cassette containing the neomycin resistance (ncor) gene under the control of the PGK promotor was introduced into the NotI site of the construct to provide pD7H15/neo. The neor cassette was cloned in the opposite direction as the DAT gene, and DNA sequencing was used to insure that pD7H15/neo did not contain a consensus start site that could be used to resume DAT translation. pD7H15/neo was linearized with AatII prior to electroporation into ES cells. Cell culture, electroporation of E14TG2a ES cells (M. Hooper et al., *Nature* 326, 292–295 (1987)) and generation of chimeric mice were performed in accordance with known techniques (B. Kohler and O. Smithies, *Proc. Natl. Acad. Sci. U.S.A.* 86, 8932–8935 (1989)). For Southern analysis, 5–15 $\mu$g DNA from ES cells or tail biopsies were digested with EcoRI and HindIII and probed with a 1.1 kb genomic DNA probe, and a neor probe to ensure that there was only one copy of the construct in ES cells. About 20%. of the tested ES cells were positive for homologous recombination, and three clones were selected for karyotyping and injection into C57/B6J blastocysts. Chimeric males were mated with C57/B6J females, and agouti coat pups were typed by Southern blotting of tail biopsies. Two germ-line transmitting males (from different ES clones) were used as colony founders. For in situ hybridization, mice were sacrificed by decapitation and the brains were dissected out, immersed overnight in 1% paraformaldehyde and cryoprotected in 15% sucrose-PBS buffer for 6–8 hours. The brains were then frozen in liquid nitrogen and cut into frontal sections (12$\mu$m) which were stored at −80° C. until required. The in situ hybridization procedure was performed with oligonucleotide probes, labeled by tailing with [$^{35}$S] dATP (NEN), with a specific activity of $2\times10^9$ cpm/$\mu$g as previously described (M. Jabar et al., *Mol. Brain Res.,* 23, 14–20 (1994); F. Tison et al., *Neurosci. Lett.* 166 48–50 (1994)). Sections were exposed at room temperature to X-ray films (Kodak X-Omat) for 7 days. Autoradiograms were scanned (Howtek Scanner) at 1200 dpi and analyzed (NIH-Image). Probe concentration and exposure times were chosen in order to stay within a linear range of detection. Experiments were performed in duplicate, and comparisons were made between groups using the Student's t test with the control value ($DAT^{+/+}$) set equal to 1, and $DAT^{+/-}$ and $DAT^{-/-}$ values expressed relatively to it. For dopamine uptake experiments, two striata from one mouse were homogenized in 0.5 ml of 0.3M sucrose and synaptosomes were prepared as described (C. Pifl et al., *J. Neurosci.* 13, 4246–4253 (1993)). The synaptosomal preparation (20–25 $\mu$g protein/tube) was incubated with 0.25 $\mu$Ci of [$^3$H] dopamine (51 Ci/mmol), and increasing concentrations of dopamine (0.3 $\mu$M) for 5 min. at 37° C. in a final volume of 0.5 ml uptake buffer (4 mM TrisHCI, 6.25 mM HEPES, 120 mM NaCl, 5 mM KCl, 1.2 mM $CaCl_2$, 1.2 Mm $MgSO_4$, 5.6 mM D-glucose, 0.5 mM ascorbic acid, pH, 7.1). Experiments were done in triplicate for each concentration, and non-specific uptake was determined in the presence of 30 $\mu$m nomifensine. Uptake was stopped and counted as described (C. Pifl et al., *J. Neurosci.* 13, 4246–4253 (1993)). $K_M$ and Vmax were calculated by the iterative curve-fitting programs EBDA and LIGAND, (G. McPherson, *J. Pharmacol. Methods* 14, 213–228 (1985)) and resulting values of three separate mice per group were averaged.

The homozygote ($DAT^{-/-}$) mice showed the expected pattern of gene disruption as established by Southern blotting. No mRNA encoding the DAT was detected in the dopamine neurons of the ventral tegmental area (VTA) and the substantia nigra compacta (SNC) of homozygote animals as demonstrated by in situ hybridization. Striatal synaptosomal preparations from $DAT^{-/-}$ mice show significant dopamine uptake as compared to wild type and heterozygote ($DAT^{+/-}$) animals. Interestingly, the heterozygote mice show a substantial decrease in the DAT mRNA (70% approx.) and a decrease in dopamine uptake (30% approx.). These data demonstrate that we have efficiently impaired the dopamine uptake activity in DAT homozygote mice. Furthermore, it appears that despite the absence of expression of the DAT in homozygote animals ever since early embryonic stages there is no compensatory expression of other monoamines transporters, such as norepinephrine and serotonin, and that these transporters have no or insignificant participation in normal dopamine uptake in the basal ganglia.

EXAMPLE 2

Weight Gain and Development of Treated Animals

Homozygotes are viable but gain weight more slowly than heterozygote and wild type ($DAT^{+/+}$) mice. They show a significant propensity for premature death when compared to wild type and heterozygotes. These two findings may be linked to an impairment in food intake, as blockade of the DAT following cocaine treatment has been associated with modification of dietary habits (R. Byck and C. VanDyke, in: *NIDA monograph* 13, 97–118 (1977)). $DAT^{-/-}$ mice are fertile and mate, but the females usually have an impaired maternal behavior, as offspring have to be transferred to foster mothers in order to be successfully raised to adulthood. This observation is consistent with the known role of dopamine on pituitary gland function and supports the controversial notion that the DAT plays a role in the regulation of the tuberoinfundibular dopamine pathway (B. Meister amd R. Elde, *Neuroendocrinology* 58, 388–395 (1993); M. Baumann and R. Rothman, *Brain Res.* 608, 175–179 (1993)). It may also be related to general modifications of cognitive or affective functions under dopaminergic influence. Previous reports indicate that cocaine treatment, which blocks the DAT, significantly modifies maternal behavior in rats (C. Kinsley et al., *Pharmacol. Biochem. Behav.* 47, 857–864 (1994); B. Zimmerberg and M. Gray, *Physiol. Behav.* 52, 379–384 (1992)).

EXAMPLE 3

Spontaneous Motor Activity in Treated Animals

The DAT is believed to play a major role in the control of locomotor behavior by regulating dopaminergic tone in the basal ganglia. Indeed, drugs that interfere with dopamine re-uptake, such as the psychostimulants cocaine and amphetamine, are know to increase locomotor behavior (A. Dahlstrom and K. Fuxe, supra; G. DiChiara and A. Imperato, supra; B. Giros and M. Caron, supra; M. Ritz et al., supra; M. Jaber et al., *Neuroscience,* 65, 1041–1050 (1995); P. Kelly et al., *Brain Res.* 94, 507–522 (1975)) accordingly, locomotor activity in DAT mice prepared as described in Example 1 above was investigated.

Mice were maintained in standard housing conditions (12 hr light/dark cycle) and were allowed free access to food and water. They were housed in groups of 6 and used between the age of 6–10 weeks. Locomotor activity was measured in Plexiglass boxes (217×268×104 mm) with 2 photocell beams located across the long and the short axis respectively, 15 mm above the floor. Activity boxes were localized in dark cabinets (6 boxes/cabinet,6 cabinets) in a quiet room, and the 3 groups of mice were always analyzed at the same time. Placement of the mice and recording of the activity numbers were done in double-blind fashion. Saline solution, cocaine (40 mg/kg) or d-amphetamine (10 mg/kg) were injected by the intra-peritoneal route (10ml/kg). Statistical analysis were performed using the Student's t test.

We find that the spontaneous locomotor activity of naive homozygotes (i.e. non-habituated to the test) is highly elevated. They have a half-time of habituation twice as long (90 min. v. 40 min.) as the wild type or heterozygote mice, and are 5 to 6 times more active than wild type during both phases of the light-dark cycle.

The heterozygotes are consistently more active that the wild type animals but this increase is of marginal significance (P=0.06) during the dark phase of the cycle. On the other hand, neither the heterozygotes nor the homozygotes exhibit a significantly enhanced level of spontaneous verticalizations or stereotypics (sniffing, grooming or rearing). It is well established that psychostimulants like amphetamine cause stereotyped behaviors by increasing extracellular dopamine in the dorsal striatum and enhance locomotor activity by increasing dopamine in the nucleus accumbens (P. Kelly et al., supra). It is interesting to note that DAT levels are substantially lower in the accumbens as opposed to the striatum in rats (J. Marshall et al., *J. Neuroscience* 37, 11–21 (1990)). Therefore, the observation of hyperlocomotion in the absence of stereotyped behavior in homozygote animals may reflect a regional difference in adaption to increased dopamine tone.

Since homozygotes lack one of the major targets of psychostimulant drugs we investigated the locomotor effect of treatment with either cocaine or amphetamine. We found that i.p. injections of high doses of cocaine (40 mg/kg) and d-amphetamine (10 mg/kg) have no significant effects on $DAT^{-/-}$ mice. On wild type and heterozygote mice, treatment with either of these two psychostimulants produces a 6 to 8 fold rise in their locomotor activity; a level that is not significantly different from the spontaneous activity in the homozygote mice. These findings directly demonstrate the major role of the DAT in the locomotor effects of psychostimulants, and rule out the participation of other monoamine transporters in these effects.

EXAMPLE 4

Effect on Genes Known to Respond to an Increase in Dopamine Levels

Dopamine exerts a modulatory control on dopaminergic and dopaminoceptive cells at the pre- and post-synaptic level (M. Jaber et al., *Neuroscience,* 65, 1041–1050 (1995); M. Jabar et al., *Mol. Brain Res.,* 23, 14–20 (1994); C. Gerfen et al., *J. Neurosci.* 11 1016–1031 (1991); C. Gerfen et al., *Science,* 250, 1429–1432 (1990)). An increase in dopaminergic transmission following psychostimulant treatment induces modifications in gene expression in cells known to be under dopaminergic control (M. Jaber et al., supra). Given the dramatic increase in spontaneous locomotor activity observed in the homozygote mice, we examined whether this hyperactivity correlated with changes in the expression of genes known to respond to an increase in dopamine levels.

In the basal ganglia, preproenkephalin A (PPA), which is co-expressed with D2 receptors, (C. LeMoine et al., *Science* 250, 1429–1432 (1990)) is under inhibitory influence of DA (C. Gerfen et al., *J. Neurosci.* 11 1016–1031 (1991); F. Tang et al., *Proc. Natl. Acad. Sci. U.S.A.* 80, 3841–3844 (1983)) whereas substance P (SP) and dynorphin (Dyn), which are coexpressed with D1 receptors (C. Gerfen et al., *Science,* 250, 1429–1432 (1990); C. LeMoine et al., *Proc. Natl. Acad. Sci. U.S.A.* 88, 4205–4209 (1991)), are under the excitatory influence of DA. (C. Gerfen et al. *J. Neurosci.* 11 1016–1031 (1991)).

By in situ hybridization (Table 1), we show that in homozygote mice PPA mRNA levels were greatly reduced (66%). mRNA coding for Dyn was increased by 50% while SP mRNA levels were not significantly modified. The finding that Dyn and SP mRNAs are not both up-regulated suggests that different activation pathways may exist for their respective genes. At the receptor level, we find that the mRNA coding for D1 and D2 receptors, the two major dopamine receptors in this region, were down-regulated by 55% and 45% respectively. This simultaneous decrease in D1 and D2 receptor mRNAs is unprecedented, as neither lesions nor pharmacological and behavioral manipulations of dopamine transmission have ever been shown to display a down-regulation of both mRNAs. We also detected a 50% decrease in D2 receptor gene expression in dopamine cells (SNC and VTA), indicating a putative down-regulation of D2 autoreceptors known to regulate dopamine levels and firing. For each of the investigated mRNAs, the heterozygotes always displayed intermediate values between the wild type and the homozygote mice (Table 1).

TABLE 1 mRNA quantification of in situ hybridization autoradiograms obtained for various genes under dopamine influence in the Striatum and ventral midbrain (VM) of Wild Type (WT), DAT(+/−) and DAT (−/−) Mice.

| Region | Gene | WT | DAT(+/−) | DAT(−/−) |
|---|---|---|---|---|
| Striatum | PPA | 1 ± 0.08 | 0.83 ± 0.07* | 0.33 ± 0.05*** |
| | SP | 1 ± 0.08 | 0.96 ± 0.07 | 1.17 ± 0.1 |
| | dyn | 1 ± 0.07 | 1.37 ± 0.09** | 1.48 ± 0.09*** |
| | $D_1R$ | 1 ± 0.08 | 0.66 ± 0.06** | 0.44 ± 0.04*** |
| | $D_2R$ | 1 ± 0.09 | 0.74 ± 0.07** | 0.56 ± 0.05*** |

TABLE 1-continued mRNA quantification of in situ hybridization autoradiograms obtained for various genes under dopamine influence in the Striatum and ventral midbrain (VM) of Wild Type (WT), DAT(+/−) and DAT (−/−) Mice.

| Region | Gene | WT | DAT(+/−) | DAT(−/−) |
|---|---|---|---|---|
| VM | DAT | 1 ± 0.08 | 0.31 ± 0.05*** | ND |
| | $D_2R$ | 1 ± 0.02 | 0.74 ± 0.05* | 0.52 ± 0.06*** |

Six mice per group were analyzed (methods in FIG. 1), and experiments performed in duplicate or triplicate. Values were compared using the Student's t test:
*: P < 0.05;
**: P < 0.01;
***: P < 0.0001;
ND, Not Detectable.

The changes in gene expression that we observed are reflective of a functional increase in dopaminergic neurotransmission and correlate with the marked increase in spontaneous locomotor activity. Moreover, these observations show that the dopamine system is able to undergo profound gradual adaptation and plasticity to an extent that has not been previously observed with pharmacological manipulations.

The foregoing examples are illustrative of the present invention, and are not to be construed as limiting thereof. The invention is defined by the following claims, with equivalents of the claims to be included therein.

That which is claimed is:

1. A recombinant mouse whose cells contain a pair of genomic dopamine transporter protein alleles, wherein both alleles are disrupted and do not express endogenous dopamine transporter protein;

and wherein said mouse has a phenotype of increased spontaneous motor activity as compared to wild-type mice.

2. A method of screening a compound for appetite modulating activity, comprising:

administering a test compound to a recombinant mouse according to claim 1; and then detecting the presence or absence of appetite modulating activity in said mouse.

3. A method according to claim 2, wherein said activity is increased appetite.

4. A method according to claim 2, wherein said activity is decreased appetite.

5. A method of screening a compound for aggressive behavior modulating activity, comprising:

administering a test compound to a recombinant mouse according to claim 1; and then detecting the presence or absence of aggresive behavior modulating activity in said mouse.

6. A method according to claim 5, wherein said activity is increased aggresive behavior.

7. A method according to claim 5, wherein said activity is decreased aggressive behavior.

* * * * *